(12) United States Patent
Kohyama

(10) Patent No.: US 8,784,326 B2
(45) Date of Patent: Jul. 22, 2014

(54) METHOD OF MANUFACTURING CORE OF CUFF FOR BLOOD PRESSURE METER AND CUFF FOR BLOOD PRESSURE METER

(75) Inventor: Takuro Kohyama, Nishitokyo (JP)

(73) Assignee: Citizen Holdings Co., Ltd., Nishitokyo-shi (JP)

(*) Notice: Subject to any disclaimer, the term of this patent is extended or adjusted under 35 U.S.C. 154(b) by 1484 days.

(21) Appl. No.: 12/225,316

(22) PCT Filed: Jan. 16, 2007

(86) PCT No.: PCT/JP2007/050450
§ 371 (c)(1),
(2), (4) Date: Sep. 18, 2008

(87) PCT Pub. No.: WO2007/116588
PCT Pub. Date: Oct. 18, 2007

(65) Prior Publication Data
US 2010/0249618 A1   Sep. 30, 2010

(30) Foreign Application Priority Data

Mar. 31, 2006   (JP) ................................ 2006-098960

(51) Int. Cl.
*A61B 5/02*   (2006.01)
*A61B 3/12*   (2006.01)
*A61B 5/022*   (2006.01)

(52) U.S. Cl.
CPC .................. *A61B 5/02233* (2013.01)
USPC ............ 600/497; 600/485; 600/489; 600/499

(58) Field of Classification Search
CPC ....... A61B 5/02; A61B 5/021; A61B 5/14551
USPC ................... 600/499, 485, 489, 497
See application file for complete search history.

(56) References Cited

U.S. PATENT DOCUMENTS

| 5,840,037 | A | * | 11/1998 | Tochikubo et al. | ........... 600/499 |
| 6,932,773 | B2 | | 8/2005 | Inoue et al. | ............... A61B 5/02 |
| 7,144,374 | B2 | * | 12/2006 | Sano et al. | ..................... 600/499 |
| 7,527,596 | B2 | | 5/2009 | Ghigini | ..................... A61B 5/00 |

FOREIGN PATENT DOCUMENTS

| EP | 1 013 220 | | 6/2000 |
| EP | 1013220 | A1 * | 6/2000 |
| JP | H05-095920 | | 4/1993 |

* cited by examiner

*Primary Examiner* — Hong Sang
(74) *Attorney, Agent, or Firm* — Manabu Kanesaka

(57) ABSTRACT

It is an object to provide a method of manufacturing a core of a cuff for blood pressure meter and a cuff for blood pressure meter in order to improve operability during the insertion and removal of an arm and fittability during the tightening of the arm as well as to enable the reduction of manufacturing costs. A cuff for blood pressure meter (1) has an air bag (12), and a core (2) disposed outside the air bag (12). The core (2) includes a flexible sheet-like first core (21) and a second core (22) which is formed into a curved shape and which is attached to and stacked on the first core (21) and which curves the first core (21).

8 Claims, 6 Drawing Sheets

METHOD OF MANUFACTURING CORE OF CUFF FOR BLOOD PRESSURE METER AND CUFF FOR BLOOD PRESSURE METER

TECHNICAL FIELD

The present invention relates to a method of manufacturing a core of a cuff for blood pressure meter and a cuff for blood pressure meter. More particularly, this cuff for blood pressure meter uses a core produced by stacking and joining a flexible sheet-like first core and a second core molded into a curved shape. This facilitates the insertion and removal of an arm and improves the fittability to the arm.

BACKGROUND ART

Recently, blood pressure meters have come into wide use in general households for the purpose of health care. A blood pressure meter for the general households typically comprises a measurement unit for automatically measuring and displaying a blood pressure, and a cuff for blood pressure meter including an air bag and so on. The measurement unit has enabled a blood pressure to be measured in a short time and with ease. However, it has been most troublesome for a user of the blood pressure meter to wind the cuff for blood pressure meter around the arm or remove the cuff for blood pressure meter from the arm.

Therefore, various techniques have been developed to improve such troublesome tasks and enable, for example, even an elderly person to easily make a measurement by himself.

PRIOR ART EXAMPLE

For example, a cuff of blood pressure meter described in Patent document 1 comprises a curved plate of a flexible member formed into a curved shape. This curved plate becomes gradually thicker from both its ends in a curving direction to its central part. This allows the rigidity in the central part to be higher than the rigidity at both ends, so that the curved plate uniformly expands when force is applied thereto. Thus, the cuff can smoothly fit both a thin arm and a thick arm.

Patent document 1: Japanese Patent Publication Laid-open No. 2-13570

DISCLOSURE OF THE INVENTION

Problem to be Solved by the Invention

However, the cuff of blood pressure meter described in Patent document 1 has a unique shape in which the curved plate becomes gradually thicker from both its ends in the curving direction to its central part. Therefore, a plastic injection molding method is used, whereby a resin is injected into and molded in a die. The problem in this respect is that it is difficult to obtain a dimensional accuracy of thin parts at both ends in the curving direction due to the shrinkage percentage during the molding or the like. Another problem is that the costs of the die, etc. are increased and manufacturing costs can not be reduced.

Moreover, the improvement of usability is required for the cuff for blood pressure meter. It is therefore necessary to further improve operability during the insertion and removal of the arm and fittability during the tightening of the arm.

The present invention has been proposed to solve the above-mentioned problems with the conventional techniques. It is therefore an object of the present invention to provide a method of manufacturing a core of a cuff for blood pressure meter and a cuff for blood pressure meter in order to improve operability during the insertion and removal of an arm and fittability during the tightening of the arm as well as to enable the reduction of manufacturing costs.

Means for Solving the Problem

In order to achieve the foregoing object, the present invention provides a cuff for blood pressure meter comprises an air bag, and a core disposed outside the air bag, wherein the core includes: a flexible sheet-like first core; and a second core which is formed into a curved shape and which is stacked on and attached to the first core and which curves the first core.

This makes it possible to provide a core having both the flexibility of the first core and shape maintaining properties (rigidity and resilience) of the second core. It is therefore possible to maintain the substantially cylindrical shape of the core during the insertion and removal of an arm. Moreover, the fittability to various shapes of arms can be improved during the tightening of the arm.

Furthermore, the first core is preferably a flat sheet.

This makes it possible to cut and use a ready-made flat sheet, so that manufacturing costs can be reduced.

Furthermore, the longitudinal dimension of the second core is preferably shorter than the longitudinal dimension of the first core.

This makes it possible to reduce the size of the second core.

Furthermore, the substantially central part of the second core is preferably joined to the surface of the substantially central part of the first core.

This makes it possible to effectively curve the first core by both ends of the second core.

Furthermore, the cuff for blood pressure meter preferably comprises fixing means for maintaining a condition where one end of the core is wound into the other end of the core.

This makes it possible for the fixing means to be subjected to external force when air is put into the air bag.

Furthermore, the cuff for blood pressure meter preferably comprises tightening means for tightening the core onto part of a living body, and the tightening means further includes a tightening belt provided in a state wound around the outer periphery of the core.

This makes it possible to tighten the core from its entire circumferential direction when the core is tightened. Therefore, a user can tighten the core around the arm without discomfort.

Furthermore, the second core preferably has holding means for holding the tightening means.

This makes it possible to easily and firmly attach the tightening means to the core.

In order to achieve the foregoing object, the present invention provides a method of manufacturing a core of a cuff for blood pressure meter, the cuff for blood pressure meter including an air bag, and a core disposed outside the air bag, the method comprises the steps of: cutting a flexible sheet to form a first core; molding a second core which is in contact with the first core and which curves the first core; and joining the second core to the first core in a stacked state.

This makes it possible to manufacture, with ease and with low manufacturing costs, a core having both the flexibility of the first core and shape maintaining properties (rigidity) of the second core.

Furthermore, in this method, in the step of joining the second core to the first core in a stacked state, the substantially central part of the second core is preferably joined to the surface of the substantially central part of the first core.

This makes it possible to easily achieve the joining and to effectively curve the first core by both ends of the second core.

BEST MODE FOR CARRYING OUT THE INVENTION

Embodiment of Cuff for Blood Pressure Meter

One embodiment of a cuff for blood pressure meter of the present invention will hereinafter be described with reference to the drawings.

Figure 1:
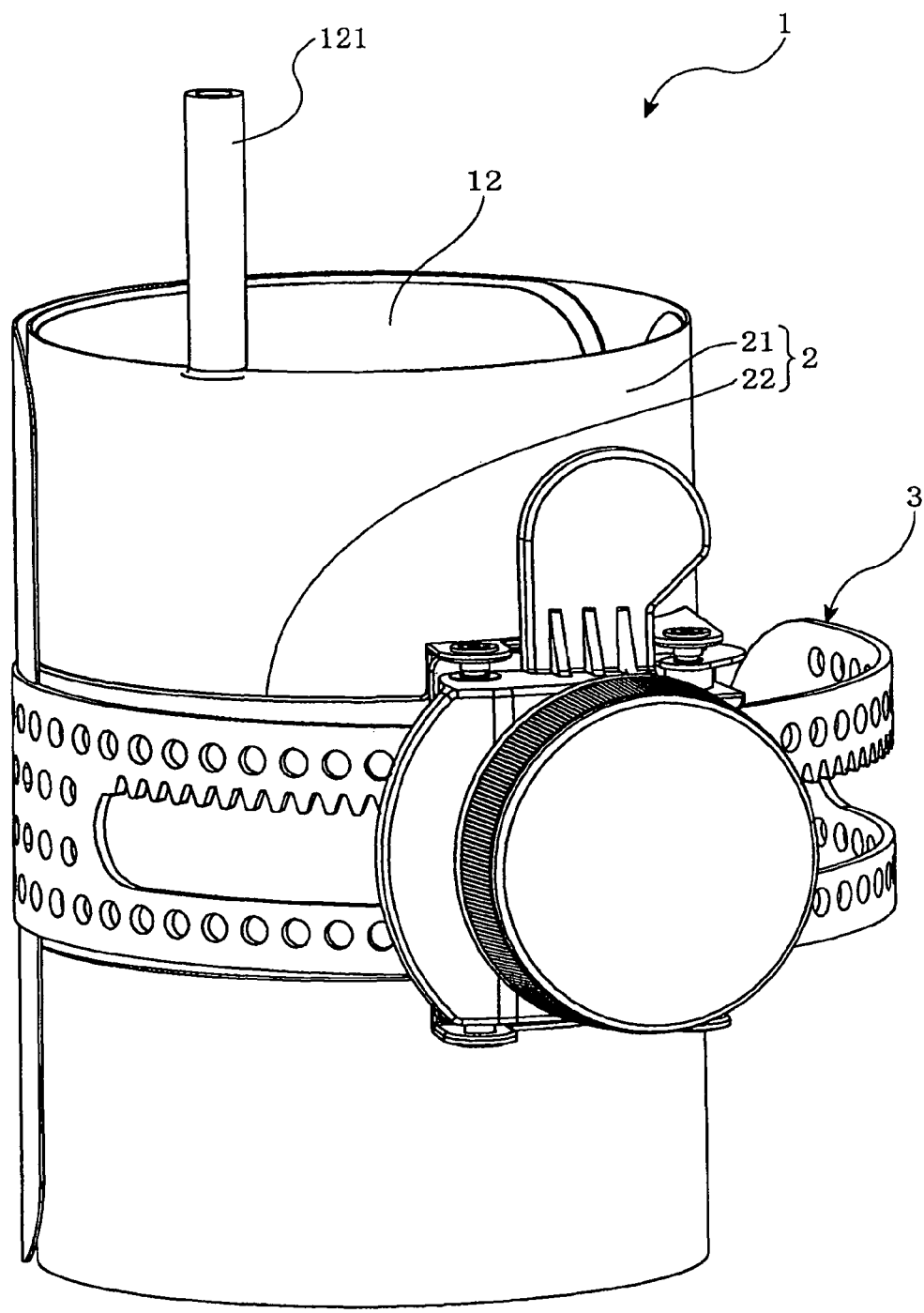
FIG. 1 shows a schematic perspective view of one embodiment of a cuff for blood pressure meter of the present invention.

FIG. 1 shows a schematic perspective view of one embodiment of the cuff for blood pressure meter of the present invention.

Figure 2:
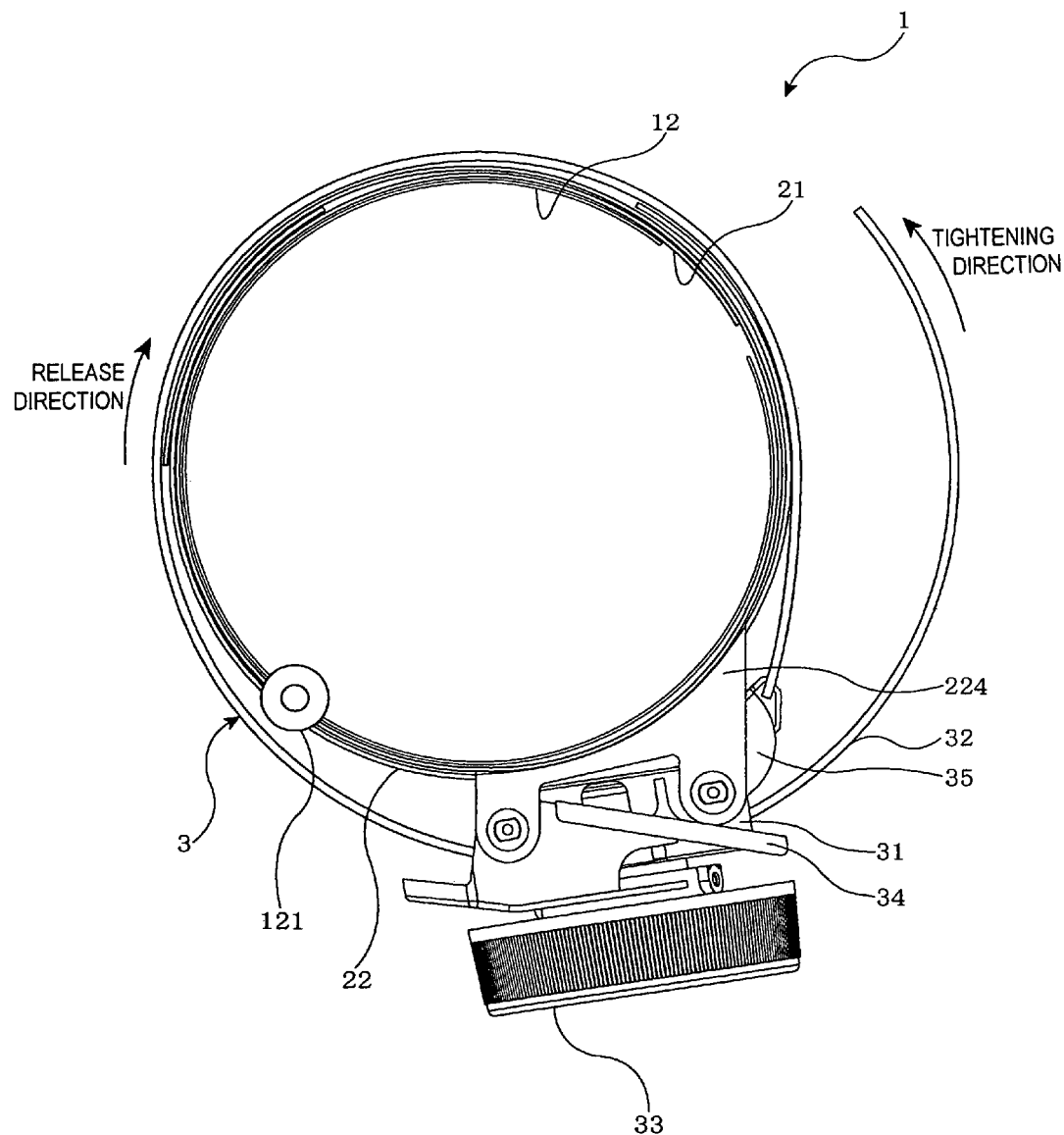
FIG. 2 shows a schematic top view of FIG. 1.
Figure 3:
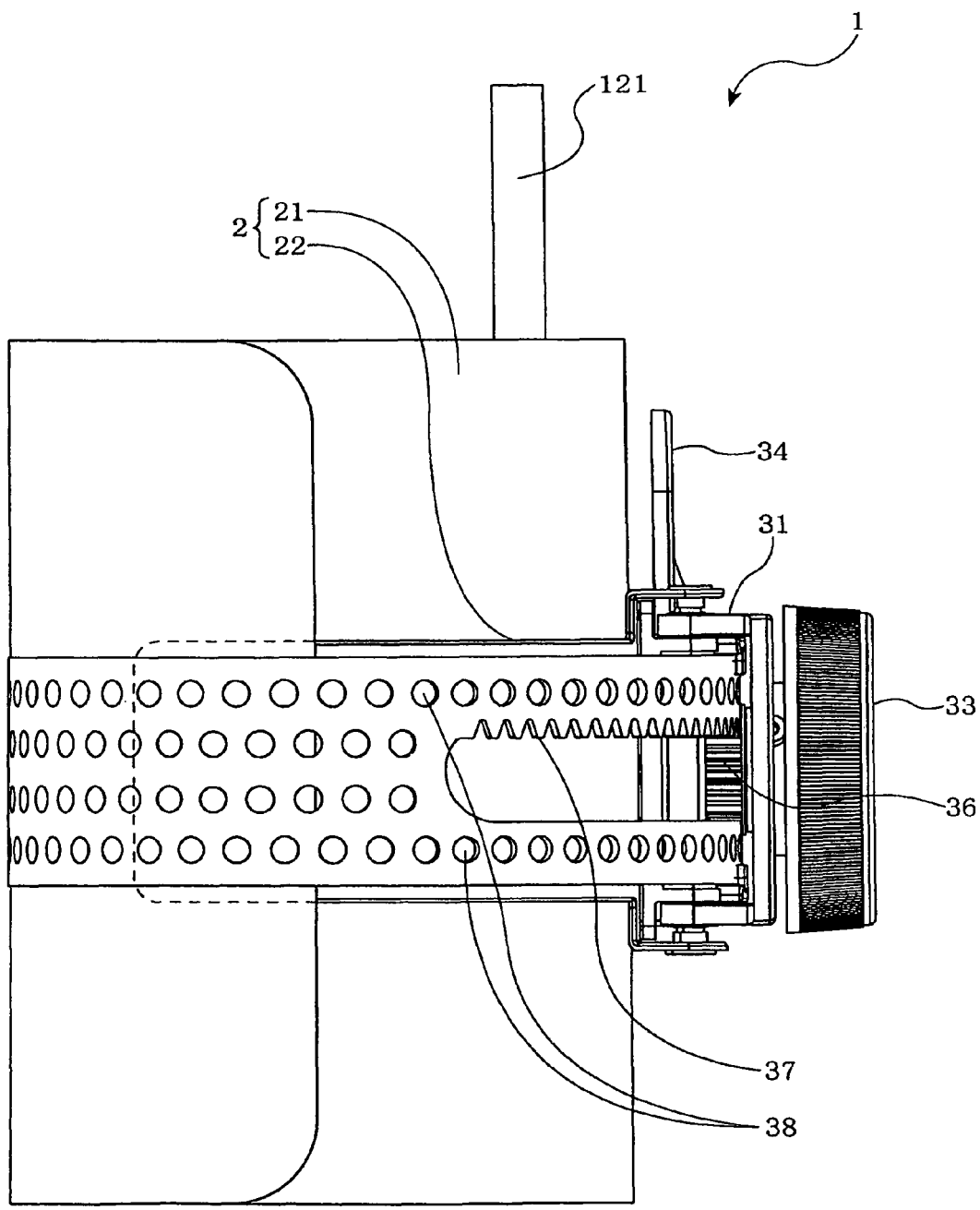
FIG. 3 shows a schematic side view of FIG. 1.

Furthermore, FIG. 2 shows a schematic top view of FIG. 1, and FIG. 3 shows a schematic side view of FIG. 1.

In FIGS. 1, 2 and 3, a cuff for blood pressure meter 1 comprises a core 2 including a first core 21 and a second core 22, tightening means 3, an air bag 12 provided with a pipe 121, etc.

The diameter of this cuff for blood pressure meter 1 is decreased by winding up the cylindrically turned core 2 when a blood pressure is measured. Thus, the core 2 is wound around an arm (not shown).

<Core>

Figure 4:
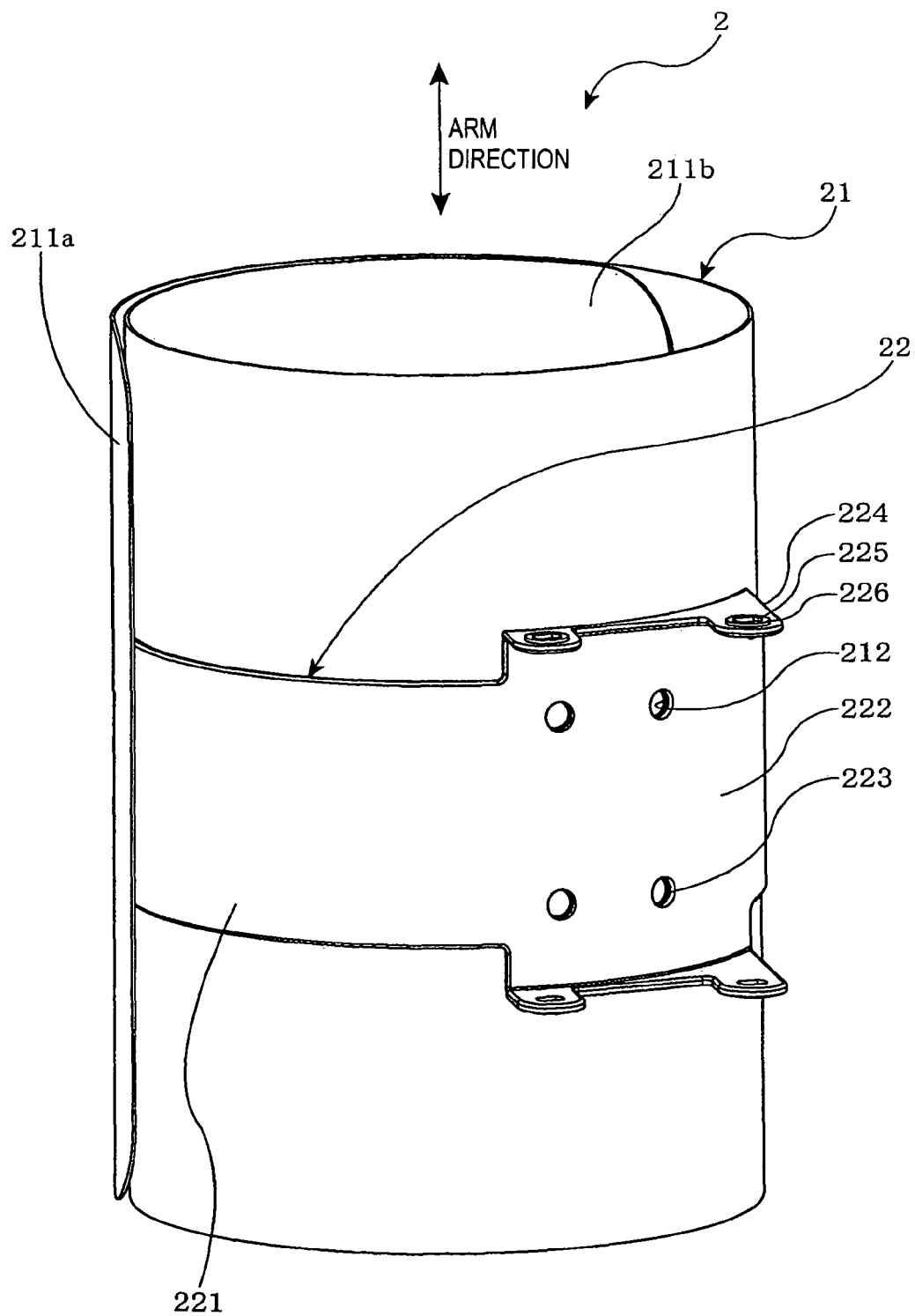
FIG. 4 shows a schematic perspective view of essential parts to explain the structure of a core according to one embodiment of the cuff for blood pressure meter of the present invention.

FIG. 4 shows a schematic perspective view of essential parts to explain the structure of a core according to one embodiment of the cuff for blood pressure meter of the present invention.

Figure 5:
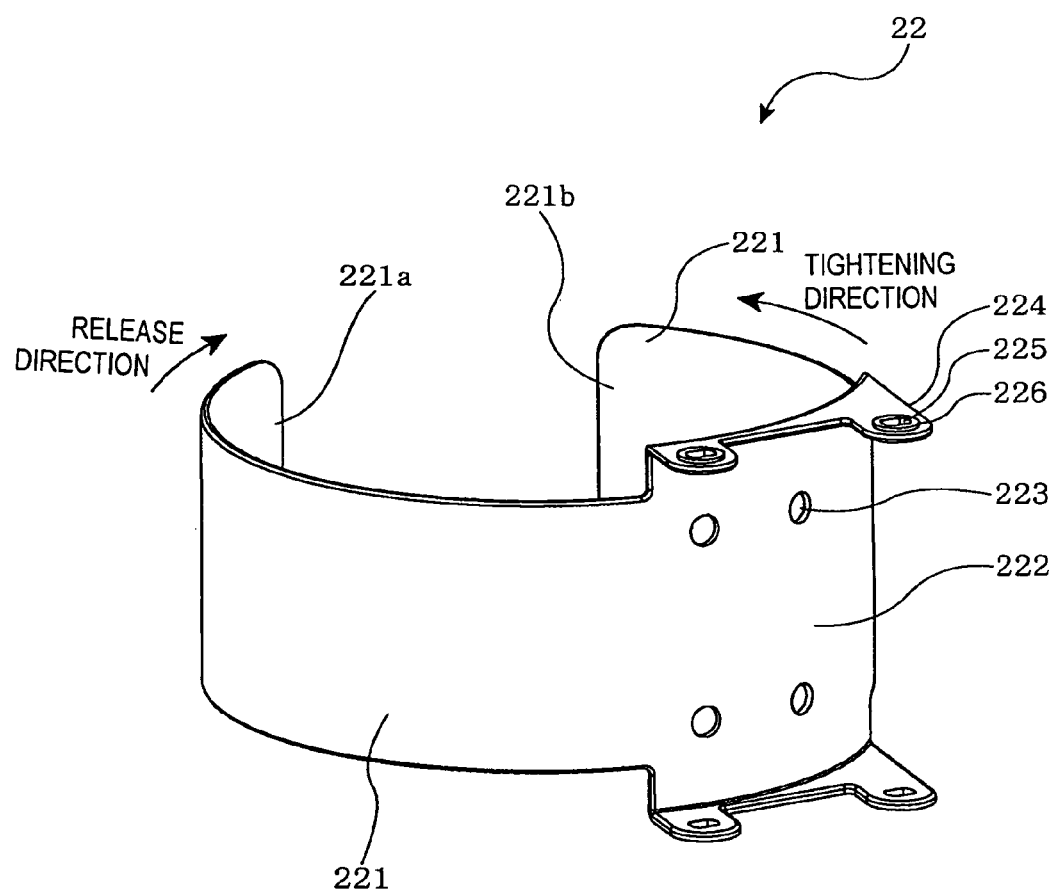
FIG. 5 shows a schematic perspective view of a second core according to one embodiment of the cuff for blood pressure meter of the present invention.

Furthermore, FIG. 5 shows a schematic perspective view of the second core according to one embodiment of the cuff for blood pressure meter of the present invention.

Figure 6:
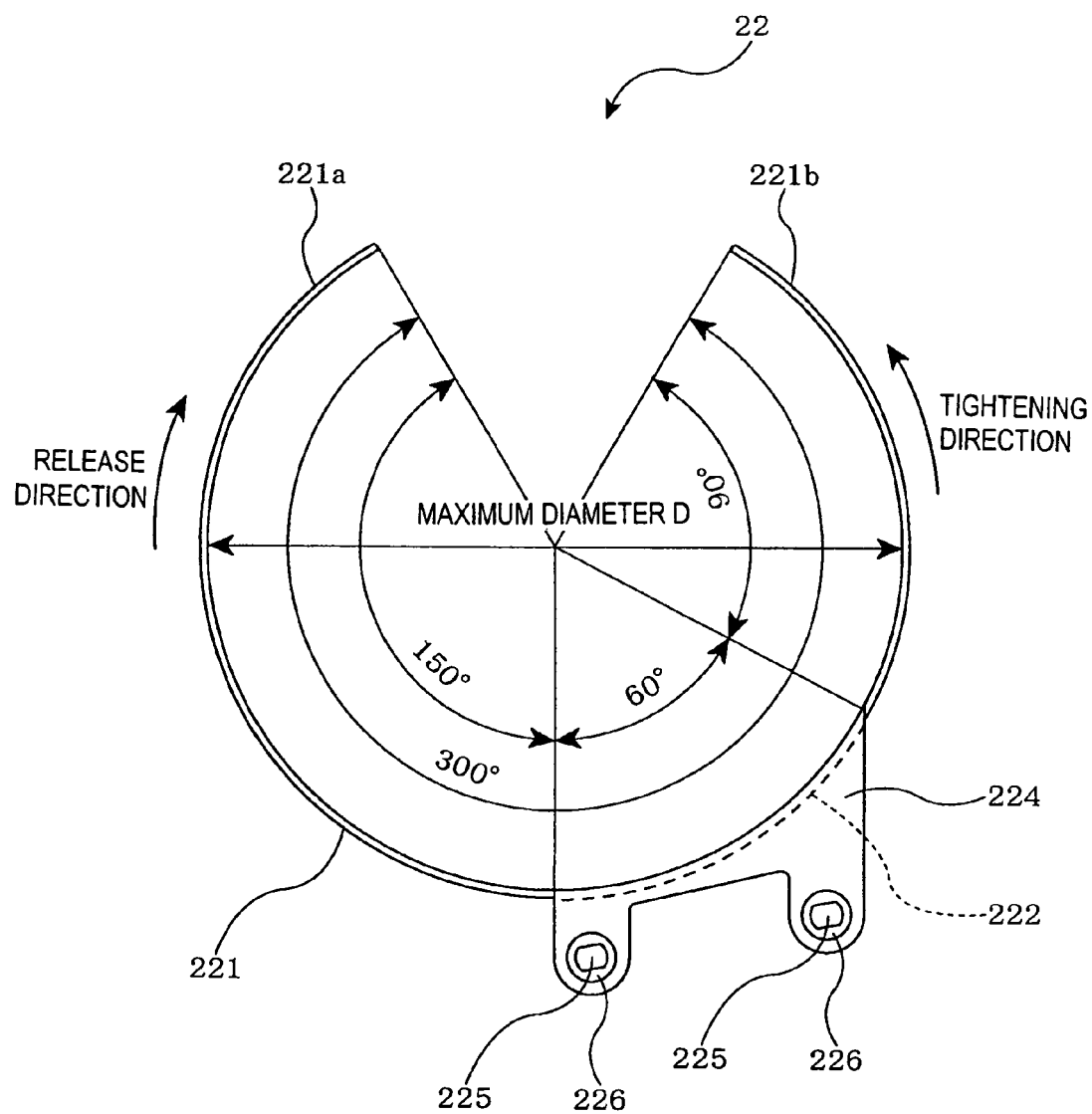
FIG. 6 shows a schematic top view of FIG. 5.

Moreover, FIG. 6 shows a schematic top view of FIG. 5.

In FIGS. 4, 5 and 6, the core 2 includes the first core 21 and the second core 22. The first core 21 is a flexible sheet. The second core 22 is formed into a curved shape, and is attached to the outside of the first core 21 so that it is stacked on the first core 21.

In addition, the second core 22 is attached to the outside of the first core 21 in the present embodiment, but the present invention is not limited to this. For example, the second core 22 may be attached to the inside of the first core 21.

The first core 21 is a resin thin flat sheet. This sheet has arc-shaped four corners, and has a substantially rectangular shape longer in a curving direction.

This first core 21 typically has a thickness of about 1 mm or several tenth mm. Thus, the first core 21 is flexibly adaptable to various shapes of arms. Moreover, the first core 21 exhibits high fittability when tightening the arm (not shown). This first core 21 has fixing holes 212 formed in its substantially central part (at positions corresponding to fixing holes 223 of the second core 22).

In the present embodiment, the material of the first core 21 is a ready-made thin flat sheet. Therefore, if this sheet is cut using, for example, a trimming die, the first core 21 can be easily manufactured. This makes it possible to reduce the manufacturing costs.

Furthermore, as compared with the case where such a thin first core 21 is manufactured by, for example, injection molding, the dimensional accuracy of thickness is improved owing to the use of the flat sheet. This makes it possible to avoid the problem of partial variations in flexibility.

When the second core 22 is joined to the first core 21 having the above-mentioned structure, an inner end 211b is wound into an outer end 211a in accordance to the curved shape of the second core 22, and overlaps the outer end 211a about 180° in the circumferential direction. The first core 21 is used in this state. Moreover, in general, the outer end 211a is curved into an arc shape outside a release side end 221a of the second core 22 by a belt 32 of the tightening means 3. That is, the first core 21 increases or decreases its diameter in accordance with the circumference of the arm while its substantially cylindrical shape is maintained by the second core 22 and the belt 32.

Furthermore, the cylindrical air bag 12 is affixed to the inner surface of the first core 21. The pipe 121 is projectingly provided in the air bag 12 in the arm direction. Air is put into the air bag 12 via the pipe 121 when the blood pressure is measured.

The second core 22 is a resin band member formed into a curved shape. The second core 22 includes a fixing plate 222, belt portions 221 and a pair of holding plates 224. The belt portions 221 extend in a release direction and a tightening direction from both side of the fixing plate 222. Moreover, the pair of holding plates 224 are projectingly provided opposite to each other from upper and lower edges of the fixing plate 222.

When viewed from above, the second core 22 has a substantially maximum diameter D (a diameter at which the arm is inserted or removed). Further, the second core 22 is formed into an arc shape over an angle of about 300°, which includes about 150° of the belt portion 221 on the side of the release direction, about 60° of the fixing plate 222, and about 90° of the belt portion 221 on the side of the tightening direction (see FIG. 6).

Furthermore, the second core 22 typically has a thickness of about several mm (e.g., 0.1 to 3 mm), and thus has sufficient shape maintaining properties (rigidity and resilience). Therefore, when the core 2 is released from the tightened and diametrically reduced state, the second core 22 is automatically restored to the maximum diameter D by its resilience. This maintains the substantially circular shape of the core 2, so that the arm can be easily inserted or removed. In addition, since the flat sheet of the first core 21 is force to curve at this moment, the first core 21 is restored by its own resilience.

The fixing plate 222 located in the substantially central part of the second core 22 is a curved rectangular plate wider than the belt portions 221 in the arm direction. The fixing plate 222 has the fixing holes 223 formed at its central four places for joining to the first core 21. This fixing plate 222 is joined to the substantially central part of the first core 21 by eyelet tacks (not shown). In addition, the first core 21 and the second core 22 are joined together using the eyelet tacks in the present embodiment, but the present invention is not limited to this. For example, they may be joined together by welding, adhesive bonding, stitching or the like.

Furthermore, the fixing plate 222 is provided with a pair of holding plates 224 as holding means for holding the tightening means 3. The pair of holding plates 224 are projectingly provided opposite to each other from the upper and lower edges of the fixing plate 222. At the ends of each of the holding plates 224 in the release direction and the tightening direction, projections 226 for reinforcing mechanical strength are formed. An elongated hole-like attachment hole 225 is formed in the projection 226. This enables the tightening means 3 to be easily and firmly attached to the core 2.

Still further, the core 2 is generally manufactured by injection molding. Moreover, the second core 22 is shorter in longitudinal dimension and smaller in size than the first core 21. This allows a die used in the injection molding to be also reduced in size, and the manufacturing costs can be reduced accordingly.

<Tightening Means>

As shown in FIGS. 2 and 3, the tightening means 3 in the present embodiment comprises a base 31, a belt 32, a knob 33, a release lever 34, a coupling plate 35, a pinion gear 36, etc.

The base 31 is fixed to the holding plates 224 of the second core 22 by, for example, bolts (not shown). This base 31 includes the rotatably attached coupling plate 35, the pinion gear 36 coupled to the knob 33, which achieves a tightening function, and attached rotatably, holding pins (not shown) achieving a holding function, the release lever 34 for releasing a state held by the holding pins, and a charging hole (not shown) into which the belt 32 is movably charged.

Furthermore, in the belt 32, a rack 37 to be geared with the pinion gear 36 is formed in the substantially central part of the width direction and in the longitudinal direction. Moreover, in the belt 32, holding holes 38 are provided side by side in the upper and lower parts of the width direction and the holding pins are engaged into the holding holes 38. One end of this belt 32 is attached to the coupling plate 35 and the other end of the belt 32 is charged into the charging hole while the belt 32 is wound around the outer periphery of the core 2. This makes it possible to tighten the core 2 from its entire circumferential direction when the core 2 is tightened, so that a user can tighten the core 2 around the arm without discomfort.

In the tightening means 3 having the configuration described above, when the user inserts the arm into the core 2 and rotates the knob 33 in the tightening direction, the pinion gear 36 acts on the rack 37. Then, the tightening means 3 moves the belt 32 in the tightening direction, and tightens the whole core 2. At this point, the holding pins are repeatedly engaged in and out of the holding holes 38 as in a ratchet mechanism. Then, when the rotation of the knob 33 is stopped, the holding pins are engaged into the holding holes 38 and hold the belt 32 so that the belt 32 may not return in the release direction. When the measurement of the blood pressure is finished and the user presses down the release lever 34, the holding pins are pulled from the holding holes 38. Then, the core 2 is automatically expanded to the maximum diameter D mainly by the resilience of the second core 22.

In addition, the tightening means 3 in the present embodiment has a function as fixing means for maintaining a condition where one end of the core 2 is wound into the other end of this core 2, and a function for tightening the core 2 around the arm. However, the present invention is not limited to this configuration. For example, it is also possible to have a simple configuration using fixing means such as a hook-and-loop fastener.

The use and operation of the cuff for blood pressure meter 1 having the above-mentioned configuration is described.

First, the user of the cuff for blood pressure meter 1 who is to have the blood pressure measured presses down the release lever 34. Thus, in the cuff for blood pressure meter 1, the belt 32 moves in the release direction by the resilience of the core 2, and the diameter of the core 2 increases to the maximum diameter D.

Subsequently, the user lays the cuff for blood pressure meter 1 on its side so that the knob 33 is directed upward, and inserts, for example, the left arm into the air bag 12.

Then, the user rotates the knob 33 in the tightening direction. Owing to this operation, the pinion gear 36 sends the rack 37 in the tightening direction, and the holding pins are repeatedly engaged in and out of the holding holes 38, and then the belt 32 moves in the tightening direction. This decreases the diameters of the core 2 and the air bag 12. Subsequently, the user tightens the core 2 up to a state that enables a measurement, and then stops the rotation of the knob 33. When the rotation of the knob 33 is stopped, the holding pins are engaged into the holding holes 38, and hold the core 2 in a satisfactory tightened state. Here, the core 2 is equipped with the suitably flexible first core 21, and can therefore fit various shapes of arms.

Then, air is put into the air bag 12, and the blood pressure is measured. Subsequently, the measurement of the blood pressure is displayed, and the air is removed from the air bag 12. Then, the user presses down the release lever 34. Thus, in the cuff for blood pressure meter 1, the belt 32 moves in the release direction by the resilience of the core 2, and the diameters of the core 2 and the air bag 12 increase. At this point, the expanded state of the cuff for blood pressure meter 1 is held by the second core 22 having the sufficient shape maintaining properties (rigidity). Therefore, the user can easily remove the arm from the core 2, and can easily insert the arm at the next measurement.

As described above, the core 2 of the cuff for blood pressure meter 1 in the present embodiment includes the flexible first core 21 and the second core 22 having the shape maintaining properties, and thus has both the flexibility and the shape maintaining properties. Consequently, the cuff for blood pressure meter 1 allows easy insertion and removal of the arm. Moreover, the cuff for blood pressure meter 1 has improved fittability to various shapes of arms when tightening the arm.

Embodiment of Method of Manufacturing Core of Sphygmomanometer Cuff

The present invention is also effective as an invention for a method of manufacturing the core of the cuff for blood pressure meter.

Next, one embodiment of the method of manufacturing the core of the cuff for blood pressure meter is described.

The method of manufacturing the core of the cuff for blood pressure meter in the present embodiment is a method of manufacturing the above-mentioned core 2 of the cuff for blood pressure meter 1. First, the flexible sheet is cut to form the first core 21 (step S1). Here, a commercially available flat sheet should be used as the above-mentioned sheet. This makes it possible to manufacture the first core 21 by simply cutting the sheet, so that the manufacturing costs can be reduced. Moreover, even if this thin sheet is manufactured by an injection molding method, the dimensional accuracy of thickness decreases due to the small thickness. Thus, the flexibility partly varies, and the fittability decreases. On the contrary, the ready-made thin flat sheet has a high dimensional accuracy of thickness, so that the problem of the decreased fittability can be avoided.

Then, the second core 22 which is to be in contact with the first core 21 and which curves the first core 21 is molded (step S2).

This core 2 is generally manufactured by injection molding, and the second core 22 is shorter in longitudinal dimension and smaller in size than the first core 21. This allows a die used in the injection molding to be also reduced in size, and the manufacturing costs can be reduced accordingly.

Furthermore, the second core 22 maintains the curved state of the first core 21.

Still, further, the second core 22 is reduced in diameter by the tightening means 3, and untightened after the measurement of the blood pressure. At this point, the second core 22 expands to the maximum diameter D by sufficient resilience. Then, the second core 22 maintains this state.

Then, the second core 22 is joined to the first core 21 in a stacked state as described above (step S3). This joining can be easily achieved by using, for example, the eyelet tacks.

Moreover, here, the substantially central part of the second core 22 is preferably fixed to the substantially central part of the first core 21. This makes it possible to easily achieve the joining and to effectively curve the first core 21 by both ends of the second core 22.

Thus, according to the method of manufacturing the core of the cuff for blood pressure meter in the present embodiment, it is possible to manufacture, with ease and with low manufacturing costs, the core 2 having both the flexibility of the first core 21 and the shape maintaining properties (rigidity) of the second core 22.

The preferred embodiments have been shown and described in connection with the method of manufacturing the core of the cuff for blood pressure meter and with the cuff for blood pressure meter. However, the method of manufacturing the core of the cuff for blood pressure meter and the cuff for blood pressure meter according to the present invention are not exclusively limited to the embodiments described above, and various modifications can be made within the scope of the present invention.

For example, while part of the second core 22 is joined to the first core 21 in the embodiments described above, the present invention is not limited to this. For example, a structure and a method can be provided wherein the second core 22 is substantially entirely joined to the first core 21.

Furthermore, while the core 2 includes the first core 21 and the second core 22 in the embodiments described above, the present invention is not limited to this. For example, a third member having an auxiliary function can be stacked between the first core 21 and the second core 22 to form a multilayer structure (structure having three or more layers).

The invention claimed is:

1. A cuff for blood pressure meter, comprising:
an air bag;
a core disposed outside the air bag including
a flexible sheet-like first core, and
a second core which is formed into an arc shape over an angle of about 300°, which is stacked on and attached to the first core, and which curves the first core;
fixing means for maintaining a condition where one end of the first core is wound into other end of the first core; and
tightening means for tightening the first core and the second core onto a part of a living body including
a tightening belt provided in a state wound around an outer periphery of the first core or the second core,
a knob, and
a release lever,
wherein
the second core has a shape maintaining property such that a maximum diameter of the second core is automatically restored by a resilience of the shape maintaining property when the second core is released from a tightened and diametrically reduced state, the second core has a fixing plate fixed onto an outer surface of the first core, and two belt portions extending from the fixing plate and the belt portions having a width shorter than a width of the first core.

2. The cuff for blood pressure meter according to claim 1, wherein the first core is made of a flat sheet.

3. The cuff for blood pressure meter according to claim 1, wherein a longitudinal dimension of the second core is shorter than a longitudinal dimension of the first core.

4. The cuff for blood pressure meter according to claim 1, wherein a central part of the second core is joined to a surface of a central part of the first core.

5. The cuff for blood pressure meter according to claim 1, wherein the second core has holding means for holding the tightening means.

6. The cuff for blood pressure meter according to claim 1, wherein the second core is made of resin.

7. The cuff for blood pressure meter according to claim 1, wherein the arc shape over the angle of about 300° includes
about 150° of the belt portion on the side of the release direction,
about 60° of the fixing plate, and
about 90° of the belt portion on the side of the tightening direction.

8. The cuff for blood pressure meter according to claim 1, further comprising a fixing device disposed outside the second core,
wherein
the fixing device has a base attached to the fixing plate of the second core, the tightening belt extending from the base to wrap around the first and second cores and having a rack, and a gear attached to the base and engaging the rack for tightening the tightening belt.

* * * * *